(12) United States Patent
Eva

(10) Patent No.: US 9,036,152 B2
(45) Date of Patent: May 19, 2015

(54) METHOD AND APPARATUS FOR DETERMINING THE ABSORPTION IN A BLANK

(71) Applicant: CARL ZEISS SMT GmbH, Oberkochen (DE)

(72) Inventor: Eric Eva, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 14/150,552

(22) Filed: Jan. 8, 2014

(65) Prior Publication Data

US 2014/0192344 A1 Jul. 10, 2014

Related U.S. Application Data

(63) Continuation of application No. PCT/EP2012/061105, filed on Jun. 12, 2012.

(60) Provisional application No. 61/505,718, filed on Jul. 8, 2011.

(30) Foreign Application Priority Data

Jul. 8, 2011 (DE) .......................... 10 2011 078 885

(51) Int. Cl.
*G01N 21/00* (2006.01)
*G01N 21/17* (2006.01)
(Continued)

(52) U.S. Cl.
CPC .............. *G01N 21/17* (2013.01); *G01N 21/171* (2013.01); *G01M 11/0285* (2013.01); *G01M 11/0257* (2013.01); *G02B 13/143* (2013.01)

(58) Field of Classification Search
CPC ............ G01N 21/1702; G01N 21/171; G01N 21/1717; G01N 21/255; G01N 29/2418
USPC ........................................................ 356/432
See application file for complete search history.

(56) References Cited

U.S. PATENT DOCUMENTS

| 4,521,118 A | 6/1985 | Rosencwaig |
| 6,065,842 A | 5/2000 | Fink |

(Continued)

FOREIGN PATENT DOCUMENTS

| DE | 101 39 906 A1 | 6/2002 |
| DE | 10 2006 014 510 A1 | 10/2006 |

(Continued)

OTHER PUBLICATIONS

Hartmann—Shack Wavefront Analyzer, Specifications, 2 pgs.

(Continued)

*Primary Examiner* — Tarifur Chowdhury
*Assistant Examiner* — MD Rahman
(74) *Attorney, Agent, or Firm* — Edell, Shapiro & Finnan, LLC

(57) ABSTRACT

A method for determining the absorption of a blank (2) for producing an optical element (3), including: radiating a heating light ray (8) through the blank (2) for the purpose of heating the blank (2), and determining the absorption in the blank (2) by measuring at least one property of a measurement light ray (10) influenced by the heating of the blank (2). In the method, either the heating light ray (8) and the measurement light ray (10) or the heating light ray and a further heating light ray are oriented to enter into the blank (2) through a first polished surface (2a) or a second polished surface (2b), situated opposite the first surface, and meet one another exclusively in the interior of the blank (2), preferably in a volume (12) used for the production of the optical element (3). An associated measuring apparatus (1), optical element (3), and optical arrangement are also disclosed.

29 Claims, 6 Drawing Sheets

(51) Int. Cl.
*G01M 11/02* (2006.01)
*G02B 13/14* (2006.01)

(56) References Cited

U.S. PATENT DOCUMENTS

| | | | |
|---|---|---|---|
| 7,436,520 B1* | 10/2008 | Doerband | 356/512 |
| 2003/0115904 A1 | 6/2003 | Kuhn et al. | |
| 2004/0036977 A1* | 2/2004 | Tanaka et al. | 359/619 |
| 2005/0057723 A1* | 3/2005 | Wakil et al. | 351/246 |
| 2005/0062971 A1 | 3/2005 | Salnik et al. | |
| 2006/0181708 A1 | 8/2006 | Takahashi et al. | |
| 2008/0316621 A1 | 12/2008 | Weber et al. | |
| 2009/0237665 A1* | 9/2009 | Wardlaw et al. | 356/432 |
| 2010/0259772 A1* | 10/2010 | Ebihara et al. | 358/1.9 |

FOREIGN PATENT DOCUMENTS

| | | |
|---|---|---|
| DE | 10 2008 048 266 A1 | 7/2010 |
| EP | 2 006 664 A2 | 12/2008 |
| EP | 2 034 363 A2 | 3/2009 |
| JP | 2005-257411 A | 9/2005 |
| JP | 2006-84431 A | 3/2006 |
| JP | 2006188424 A | 7/2006 |
| JP | 2008139200 A | 6/2008 |

OTHER PUBLICATIONS

Dorte Schoenfeld et al., "Measurement of Initial Absorption of Fused Silica at 193nm using Laser Induced Deflection Technique (LID)", SPIE Boulder Damage Symposium 2007, Sep. 25, 2007, 12 pgs.

K. Mann et al., "Photo-thermal measurement of absorption and wavefront deformations in fused silica", Laser-Laboratorium Gottingen e.V., 10 pgs.

K. Mann et al., "Characterization of absorption in deep UV optical materials", Laser-Laboratorium Gottingen e.V., 10 pgs.

B. Kuehn et al., "Minimizing Losses in Synthetic Fused Silica for Immersion Lithography", Laser-Laboratorium Gottingen e.V., 1 pg.

K. Mann et al., "A novel photo-thermal setup for determination of absorptance losses and wavefront deformations in DUV optics", Proceedings of SPIE; Laser-Induced Damage in Optical Materials 2007, Jan. 1, 2007, 10 pgs., vol. 6720.

Christian Muehlig et al., "Characterization of low losses in optical thin films and materials", Applied Optics, May 1, 2008, pp. C135-C142, vol. 47, No. 13.

Bernd Schaefer et al., "Absolute measurement of surface and bulk absorption in DUV optics from temperature induced wavefront deformation", Optics Express, Oct. 11, 2010, pp. 21534-21539, vol. 18, No. 21.

Eric Eva, "Kalorimetrische Bestimmung der UV-Strahlungsabsorption an optischen Glaesern und duennen Schichten unter besonderer Beruecksichtigung laserinduzierter Aenderungen", Laser-Laboratorium Goettingen e.V., 1994, pp. 34-37.

J. Siegel et al., "Investigation of laser-induced damage at 248 nm in oxide thin films with a pulsed photoacoustic mirage technique", Journal de Physique IV, Jul. 1994, pp. C7-745-C7-748, vol. 4.

W.B. Jackson et al., "Photothermal deflection spectroscopy and detection", Applied Optics, Apr. 15, 1981, pp. 1333-1344, vol. 20, No. 8.

C. Goerling et al., "Comparative studies of absorptance behaviour of alkaline-earth fluorides at 193nm and 157 nm", Applied Physics B 2002, pp. 259-265, vol. 74.

International Search Report for PCT/EP2012/061105 dated Sep. 21, 2012.

Eric Eva, "Kalorimetrische Bestimmung der UV-Stahlungsabsoption an optischen Gläsern und dünnen Schichten unter besonderer Berücksichtigung laserinduzierter Änderungen-Calorimetric determination of the UV radiation absorption at optical glasses and thin layers taking particular account of laser-induced changes", Laser-Laboratorium Göttingen e.V., 1994, pp. 34-37.

Office Action of German counterpart Patent Application No. DE 10 2011 078 885.9 dated Mar. 13, 2012.

English language summary of Office Action in corresponding Japanese Application No. 2014-517569, dated Feb. 10, 2015.

* cited by examiner

METHOD AND APPARATUS FOR DETERMINING THE ABSORPTION IN A BLANK

CROSS-REFERENCE TO RELATED APPLICATIONS

The present application is a Continuation of International Application No. PCT/EP2012/061105, filed on Jun. 12, 2012 claims priority under 35 U.S.C. §119(a) to German Patent Application No. 10 2011 078 885.9, filed on Jul. 8, 2011, also claims the benefit under 35 U.S.C. 119(e)(1) of U.S. Provisional Application No. 61/505,718, filed on Jul. 8, 2011. The disclosures of these three applications are hereby incorporated into the present application by reference in their respective entireties.

FIELD AND BACKGROUND OF THE INVENTION

The invention relates to a method for determining the absorption of a blank for producing an optical element, comprising: radiating a heating light ray through the blank for the purpose of heating the blank, and determining the absorption in the blank by measuring at least one property of a measurement light ray influenced by the heating of the blank. The invention also relates to an apparatus for determining the absorption of a blank for producing an optical element, comprising: a holding device for the blank, at least one heating light source for generating at least one heating light ray for heating the blank, a measurement light source for generating a measurement light ray, and a detector unit for measuring at least one property of the measurement light ray influenced by the heating of the blank. The invention furthermore relates to an associated optical element and to an optical arrangement comprising at least one such optical element.

The radiation used in optical systems for microlithography, in particular in projection exposure apparatuses or projection lenses, which is typically at an operating wavelength in the UV range (less than 250 nm), is absorbed at the surfaces and in the volume of the optical elements arranged in these systems. The material of the optical elements is heated by the absorbed radiation and expands, and the refractive index in the respective material changes in a location-dependent manner, such that a thermal lens effect ("lens heating") is associated with the change in temperature, and said thermal lens effect can lead to imaging aberrations in the optical systems.

The thermal lens effect can be compensated for actively (with manipulators), but it is more expedient to provide optical elements having reduced absorption, in order to counteract the thermal lens effect by reducing the temperature increase in the optical elements.

In the prior art, the absorption in blanks composed of a lens material transparent to wavelengths in the UV range is typically characterized in transmission. In this case, the internal absorbance coefficient k is determined, which is given by:

$$K_{int} = -\log(T_i)/d,$$

where $T_i$ denotes the internal transmission (i.e. transmission corrected by reflection losses) and d denotes the sample thickness. For the optical materials used nowadays in microlithography, the absorbance coefficient k is generally composed of a stray light component in the range of between approximately 7 and $10 \times 10^{-4}$/cm and an absorption component in the range of between 1 and $2 \times 10^{-4}$/cm. Given a sample length of typically 1 to 5 cm, an error in the transmission measurement leads to a further uncertainty of approximately $3 \times 10^{-4}$/cm in the absorbance. If, by way of example, given a sample thickness d of 3 cm and a measured absorbance coefficient of $k=1 \times 10^{-3}$/cm, a typical error $\Delta T$ in the transmission of 0.2% is assumed (owing to a fluctuation in the surface absorption and owing to the measurement error), the error $\Delta k$ in the absorbance coefficient k is $\Delta k = 2.85 \times 10^{-4}$/cm. In addition there is also the uncertainty about the scattering and absorption losses at the two surfaces of the blank. Consequently, it is virtually impossible to reliably measure a volume absorption of less than $2 \times 10^{-4}$/cm using transmission measurements.

Therefore, a method for directly determining absorption is required which ideally also allows 100% monitoring of all blanks.

A method for directly determining absorption has been disclosed, inter alia, by the publication by K. Mann, A. Bayer, T. Miege, U. Leinhos and B. Schäfer "A Novel Photo-Thermal Setup for Evaluation of Absorptance Losses and Thermal Wavefront Deformations in DUV Optics", Proceedings of the 39th Boulder Damage Symposium, Boulder, Colo. (USA), SPIE Vol. 6720, 6720-72 (2007). The photo-thermal measuring device described therein uses cylindrical blanks having a diameter of approximately 25 mm and a length of approximately 40 to 50 mm. A thin heating light ray (having a diameter of approximately 5 mm) from an excimer laser (wavelength of approximately 193 nm) is radiated through said blanks in the longitudinal direction and said blanks are heated in the process. An expanded measurement light ray from a diode laser (wavelength approximately 639 nm), which runs at a small angle (typically 5° to 10°), with respect to the heating light ray, radiates through the volume heated by the excimer laser and the optical material surrounding said volume. A Shack-Hartmann sensor analyses the wavefront of the measurement light ray that has passed through the blank. By comparing the wavefront without and with the action of the heating light ray, it is possible to determine the thermal lens effect with an accuracy of significantly better than 1 nm. Through suitable calibration (computation, electrical heating, gray sample), an absorbed energy can be assigned to the wavefront deformation and the absorptance can thus be determined with knowledge of the incident energy.

What is problematic about the above-described method with virtually collinear heating and measurement light rays is that the wavefront distortion on account of the absorption at the surfaces of the blank is also measured. This requires very careful polishing of the surfaces, which is intended to guarantee a low surface absorption that is reproducible as well as possible.

Furthermore, heretofore it has additionally been necessary to cut separate samples from the blank: since contaminations penetrate into the blank from outside during the manufacturing process, axial and radial edge regions of the blank generally have a higher absorption than the inner region and are therefore cut off before delivery. If the samples were manufactured from edge material, a systematically excessively poor measurement value would be obtained and sampling from the acceptable quality region either would not be non-destructive or would result in a great increase in production costs, since an additional diameter or an additional volume would have to be included in planning, in order to obtain high-quality and thus representative material also outside the geometry actually to be produced.

In principle, the collinear photo-thermal method described above would in principle also be possible on (entire) polished blanks if, for each blank thickness, a calibration and the measurement were carried out shortly after switching on the laser, i.e. if the input heat were still concentrated on the vicinity of the heating light ray. However, owing to the high sensitivity of the method to the surface absorption, a very complex polishing of the entire blank would be necessary, which would be very cost-intensive. Moreover, with progressive improvement in the material properties, i.e. reduction of the absorption in the volume of the blank, the point would rapidly be reached at which the surface absorption would dominate the overall signal during the measurement.

Alternatively, a direct determination of the absorption of a blank can also be carried out with an LID ("laser-induced deflection") method, as described e.g. in DE 101 399 06 A1. A cube or a parallelepiped having at least four polished surfaces is required for carrying out this method. In this case, the measurement light ray runs transversely, i.e. at an angle of approximately 90°, with respect to the heating light ray and passes the heating light ray outside the light bundle cross section thereof in the volume of the blank. The gradient in the refractive index produced by the temperature increase in the material of the blank produces a deflection of the measurement light ray, which can be detected e.g. by a quadrant diode. This method has the advantage of not being sensitive to surface absorption, but it is very sensitive to the distance between measurement light ray and heating light ray. More recently (cf. C. Mühlig et al., "Characterization of low losses in optical thin films and materials", Applied Optics, Vol. 47, Issue 13, pp. C135-C142) is has been proposed that the method be carried out with two or with four measurement light rays. Since the latter lie on both sides of the heating light ray, this method is less sensitive with respect to the relative alignment of heating light ray and measurement light rays. Nevertheless, the capture range is only approximately 1 mm, for which reason samples of fixed geometry continue to be relied on.

The article "Absolute measurement of surface and bulk absorption in DUV optics from temperature induced wavefront deformation", by B. Schäfer et al., Optics Express 2010, Vol. 18, No. 21 has also disclosed an apparatus and a method for quantitatively determining both the surface proportion and the volume proportion of the absorption of a sample. In that case, a heating light ray and a measurement light ray intersect at an angle of 90° within the sample volume, a Shack-Hartmann sensor being used to analyze the wavefront of the measurement light ray that has passed through the blank. In order to carry out an absorption measurement in a spatially resolved fashion, this method also requires highly complex polishing of the surfaces of the entire blank or an additional sample volume.

OBJECTS AND SUMMARY OF THE INVENTION

It is an object of the invention to develop a method and an apparatus of the type mentioned in the introduction in such a way as to make it possible to precisely measure the absorption in the volume of a blank with reduced outlay. It is furthermore an object of the invention to provide an optical element having a thermal lens effect that is as small as possible, in particular that is known in advance, and an optical arrangement comprising at least one such optical element.

This object is achieved, in accordance with one aspect, with a method of the type mentioned in the introduction wherein either the heating light ray and the measurement light ray or the heating light ray and a further heating light ray are oriented in such a way that they enter into the blank through a first polished surface or a second polished surface, situated opposite the first surface, and meet one another exclusively in the interior of the blank, preferably in a volume used for the production of the optical element.

The invention proposes using a measurement method wherein the measurement light ray and the heating light ray, as in the case of the photo-thermal method described above, meet one another in the volume of the blank, but the region in which the measurement light ray and the heating light ray overlap is restricted to the interior of the blank, such that the surface absorption is not measured and complex polishing of the blank or a calibration of the measurement for each geometry (blank thickness and diameter) can therefore be dispensed with. By virtue of all rays used for the measurement entering and/or exiting at only two polished surfaces situated opposite one another, the blank can be measured with a good spatial resolution without the provision of an additional measurement volume or without additional polishing. It goes without saying that in this case both rays can enter into the blank through the same polished surface. However, it is also possible for a first one of the two rays to enter into the blank through the first polished surface, while a second one of the two rays enters into the blank through the second surface, such that the two rays pass through the blank in opposite directions.

As an alternative to measuring a property of the measurement light ray in transmission, wherein the measurement light ray and the heating light ray meet in the interior of the blank, it is also possible to orient two heating light rays such that they meet in the interior of the blank, wherein in this case a property of the measurement light ray in reflection is measured, as will be explained in detail further below.

In both cases it is of advantage if the respective rays meet one another only in the volume region used for the production of the optical element, since in this way the highly absorbent edge regions of the blank, which are not used for the production of the optical element anyway, make no contribution to the measurement. As a rule of thumb, the region used for the production of the optical element, and thus the overlap region, is arranged at a distance of at least 5 mm from the surfaces of the blank.

The blank typically consists of synthetic quartz glass, which is suitable for microlithography. Such quartz glass generally has a proportion of metallic impurities of less than 10 ppb, wherein the Na content should be less than 2 ppb, the OH content should be less than 100 ppm and the H2 content should be more than $10^{16}$ molecules/cm$^3$.

The polished surfaces are typically the end faces of the generally cylindrical blank. As described in the introduction, for carrying out the method it is not absolutely necessary to produce a residual roughness as small as possible at the polished surfaces, since the surface absorption does not influence the measurement. The polishing is merely intended to ensure that the respective rays enter into the blank or emerge therefrom with sufficiently high intensity.

At least the polished surface on which the measurement light ray impinges typically has a polishing quality which, in accordance with the quality scale according to DIN ISO 10110-8, which assesses residual defects such as scores or holes, is in the range of the standard classes P1 and P2, i.e. at a comparatively simple polishing quality which is completely sufficient for the method used here. It goes without saying that alternatively it is also possible to carry out polishing up to higher polishing classes (P3 and P4), but this is not necessary and merely leads to an increase in costs. With regard to figure too, which describes the quality of the surface with regard to long-wave aberrations, comparatively low qualities, e.g. λ/5 where λ=633 nm, suffice for the photo-thermal method used here, since a reference measurement is generally carried out before the laser is started.

In one variant of the method, the heating light ray and the measurement light ray meet one another in the interior of the blank at an angle of less than 90°, preferably of less than 40°, particularly preferably of less than 30°. The angular range at which the two rays advantageously meet one another in the interior of the blank is dependent on a number of parameters, for example on the thickness of the blank and on the irradiation duration. The intersection angle of the two rays in the interior of the blank should typically also not be less than approximately 15° or than approximately 10°. In order to increase the measurement accuracy, the running length of the measurement light ray through the volume heated by the heating light ray should be as large as possible, although on the other hand a small overlap region is favorable in order to achieve a good spatial resolution. It has been found that angles within the limits indicated above are particularly advantageous for carrying out the method.

In a further variant, as a property of the measurement light ray, a wavefront deformation of the measurement light ray brought about by the heating light ray is measured in a spatially resolved fashion. In contrast to the method described in DE 101 399 06 A1 cited in the introduction, a planar measurement of the wavefront transversely with respect to the heating light ray is performed in the present case. This makes it possible to dispense with careful alignment of the rays and instead to evaluate the measured wavefront with suitable measurement software. In this case, the signal-to-noise ratio can be improved in various ways, e.g. by averaging the measured signal in parallel with the heating light ray or by periodically exciting the heating light ray. The absorption can be determined from the measured wavefront deformation for example on the basis of the maximum value of the measurement curve or the gradient or the curvature at a specific distance from the maximum.

The use of a Shack-Hartmann sensor has proved to be advantageous for measuring the wavefront deformation. The Shack-Hartmann sensor generally has an array of lens elements ("lenselets"), having an identical focal length. One simplified variant of the Shack-Hartmann sensor uses an array of pinhole diaphragms. It goes without saying that wavefront sensors of different design can also be used for measuring the wavefront, e.g. wavefront curvature sensors or, if appropriate, shearing interferometers.

In one variant of the method, the position of the overlap region, at which the measurement light ray and the heating light ray or the two heating light rays meet one another, is varied in the volume used for the production of the optical element in two dimensions, preferably in three dimensions, in order to determine the spatially resolved absorption behavior in the blank or in the optical element. On account of the measurement signal being largely independent of the alignment of the respective rays and the distance with respect to the lateral surface or the ends faces of the blank, the blank can be scanned in the optically used volume (in the xy-direction, i.e. parallel to the end faces). Given a small interaction volume between the respective rays, scanning can even be effected in the z-direction, i.e. perpendicular to the end faces, i.e. it is possible to record a depth profile of the absorption in the blank, in which case however—as described above—the edge regions of the volume of the blank are respectively excluded.

A model for the temperature-dependent variation of the optical properties of the optical element produced from the blank, in particular the temperature-dependent refractive index variation thereof, can be created from the spatially resolved absorption behavior in the blank. Partial regions of the optical element having high absorption experience greater heating than partial regions having lower absorption during irradiation, such that a greater change in the index gradient occurs there, which can be calculated with the aid of a model by way of the relationship between location-dependent absorption and index shift. In particular, a model for predicting a temporal change in the refractive index variation on account of a temperature change can be created on the basis of the spatially resolved absorption behavior. With the aid of such a model, it is possible to anticipate dynamic changes in the wavefront upon transition between different states of the optical system, e.g. of a projection lens, in which the optical element is incorporated. In this case, additional parameters of the optical system that are not dependent on the optical material used can be employed in order to obtain a predictive model for the behavior of the entire optical system in the event of temperature fluctuations. This model can be used for feed-forward compensation of the expected dynamic change or deformation of the wavefront upon transition between two system states, by virtue of manipulators present in the optical system being suitably driven (and moved) in order to compensate for the expected change in the wavefront upon transition between the system states. The system states can be e.g. different settings of an illumination system which couples illumination radiation into a projection lens.

It is of advantage to choose the diameter of the measurement light ray to be at least three, preferably at least five, times the magnitude of the diameter of the heating light ray, to be precise relative to the dimension of the measurement light ray transversely with respect to the connecting line (strictly speaking with respect to the connecting plane) between the measurement light ray and the heating light ray in the blank, such that on the detector area it is possible to detect the wavefront of the measurement light ray in a sufficiently large region around the heating light ray. The cross section of the measurement light ray can be chosen to be elliptical or rectangular, which combines a good separation of the rays near the polished surfaces with a good "fit" region for the overlap. With the use of elliptical or rectangular ray cross sections, the short ray axes of measurement light ray and heating light ray typically lie in a common plane and the long ray axes lie parallel to one another at the intersection point. The ratio of long ray axis to short ray axis should be at least 2:1 in the case of an elliptical or rectangular ray cross section, to be precise both for the heating light ray and for the measurement light ray.

For carrying out all method variants described above it is expedient if the measurement light ray and the heating light ray are at a distance of at least 5 mm from one another on the first and the second polished surface, since during irradiation in the blank a heat flow arises which has the effect that the temperature distribution in the blank drifts, to be precise by approximately 5 mm in 3 seconds, cf. page 34 and pages 36-37 of the dissertation "Kalorimetrische Bestimmung der UV-Strahlungsabsorption an optischen Gläsern and dünnen Schichten unter besonderer Berücksichtigung Iaserinduzierter Änderungen" ["Calorimetric determination of the UV radiation absorption at optical glasses and thin layers taking particular account of laser-induced changes"], by Eric Eva, Laser-Laboratorium Göttingen, LLG, 1994.

In one development of this variant, at least one property, in particular the wavefront deformation, of the measurement light ray deflected, in particular reflected, by the polished surface in a region in between the two heating light rays is measured. In this variant, the heating light rays are caused to overlap in a volume of the blank near the surface (but typically at a distance of more than 5 mm from the surfaces), such that the heating is greater in the overlap region than along the individual heating rays. The detection is effected using a bulge which is produced by the material expansion and which forms at the surface of the blank. For this purpose, the measurement light ray is oriented toward the surface in the vicinity of the bulge and the wavefront distortion is detected at the reflected measurement light ray. In this case, the diameter of the measurement light ray should be chosen such that the latter does not encompass the two entrance regions of the heating light rays at the polished surface, since considerable heating occurs there on account of the absorption at the polished surface. In the case of the measurement described above, the polishing of a second (opposite) surface of the blank can be dispensed with.

As an alternative to the reflection of the measurement light ray, the detection can also be effected with an individual measurement light ray which either strikes the flank of the bulge and is deflected there or else runs parallel to the surface and is deflected by the heating of the air (PTD and mirage method, cf. publications by C. Amra, M. Reichling and E. Welsch, e.g. "Investigation of laser-induced damage at 248 nm in oxide thin films with a pulsed photoacoustic mirage technique", Journal de Physique IV, Colloque C7, Supplement au Journal de Physique III, Vol. 4, July 1994). The use of a wavefront sensor has the advantage, however, that careful alignment is not necessary or can be replaced by suitable software adaptation.

In a further variation, the wavelength of the heating light ray deviates from the used wavelength of the optical element by less than 5 nm, wherein the used wavelength is 250 nm or less, in particular 193 nm or less. Typical wavelengths of the heating light ray are the wavelengths of approximately 248, 192, 176, 157 nm that are usually used in projection exposure apparatuses for microlithography. In order to minimize material aging and nonlinear absorption effects, beside the wavelength the irradiation parameters of the heating light ray should also be as close as possible to the use conditions in a projection exposure apparatus.

Usually, the wavelength of the measurement light ray deviates from the wavelength of the heating light ray and is preferably more than 250 nm. Although the use of a measurement light ray at short wavelengths e.g. of less than 200 nm brings about a higher sensitivity during the measurement, the use of such a wavelength for the measurement light ray typically leads to considerable experimental problems, such that a wavelength in the visible wavelength range, e.g. at 639 nm, is generally used for the measurement light ray.

In a further variant, before determining the absorption of the blank, the blank is irradiated with a predefined radiation dose. Such prior irradiation is expedient if purification effects and/or bleaching effects occur in the material of the blank, which should have concluded before the beginning of the absorption measurement. In this case, the necessary prior irradiation dose can be determined by repeated measurements until a rapid decrease in the absorption does not occur, but rather only a very slow rise as a result of material aging. The blank, at least at the locations or regions in which the absorption measurement is intended to be carried out, is then irradiated with the radiation dose thus determined before the beginning of the measurement.

In a further variant, an optical element is produced only from such blanks in which, in the entire volume used for the production of the optical element, at a wavelength of 193 nm (more precisely: 193.4 nm), an absorption coefficient $k_0$ of $2\times10^{-4}$/cm or less, preferably of $1\times10^{-4}$/cm or less, in particular of $0.5\times10^{-4}$/cm or less, is measured.

A selection of blanks which have an absorption acceptable for the respective application can be made using the measuring method described above. In this case, the partial regions of the volume used for the production of the optical element, at which partial regions the absorption is intended to be as low as possible, lie at locations at which the thermal lens effect has a particularly unfavorable effect on the (imaging) properties of the optical element. It goes without saying that if appropriate on the basis of the measurement data about the absorption in the volume of the blank, the volume region cut from the blank during the production of the optical element can also be defined such that a particularly low absorption is established in the relevant regions. In particular, on the basis of the absorption behavior it is possible to define the type of optical element for the production of which the respective blank is suitable, if appropriate, i.e. it is possible to perform an assignment between blanks and optical elements producible therefrom which meet the requirements with regard to the absorption.

A further aspect of the invention is realized in an apparatus of the type mentioned in the introduction wherein either the heating light ray and the measurement light ray or the heating light ray and a further heating light ray are oriented in such a way that they enter into the blank through a first polished surface or a second polished surface, situated opposite the first surface, and meet one another exclusively in the interior of the blank, preferably in a volume of the blank used for the production of the optical element. In order to enable a suitable orientation of the heating light rays or of the heating light ray and of the measurement light ray, both the measurement and the heating light source can be provided, if appropriate, with a (motor-driven) movement mechanism which enables a translational movement and/or a rotational movement of the respective sources.

In one embodiment, the heating light ray and the measurement light ray or the two heating light rays meet one another in the interior of the blank at an angle of less than 90°, preferably of less than 40°, in particular of less than 30°. As has already been explained further above, it is expedient for the measurement accuracy if the overlap region between the respective heating light rays is as large as possible, but a large overlap region leads to a reduction of the spatial resolution. It has been found that the angular range indicated above is particularly well suited to meeting both requirements when carrying out the method.

For the spatially resolved measurement of the blank, the holding device for the blank can be designed to be displaceable linearly in two directions, preferably in three directions. It goes without saying that a rotary drive can additionally also be provided in order to suitably orient the blank relative to the light sources.

In a further embodiment, the detector unit has a measuring device for wavefront deformation measurement, in particular a Shack-Hartmann sensor. It goes without saying that other types of wavefront detectors can also be used for wavefront measurement.

A further aspect of the invention is realized in an optical element, in particular a lens element, which, in the entire volume, has an absorption coefficient $k_0$ of $2\times10^{-4}$/cm or less, preferably of $1\times10^{-4}$/cm or less, in particular of $0.5\times10^{-4}$/cm or less, at a wavelength of 193 nm, wherein the absorption coefficient $k_0$ is determined, in particular, by a method as described above.

A further aspect of the invention is realized in an optical arrangement, in particular in a projection lens for microlithography, which comprises at least one optical element as described above.

In one embodiment, at least one optical element of the optical arrangement having a subaperture ratio of greater than 50%, preferably greater than 70%, in particular greater than 80% (in the entire volume) has an absorption coefficient $k_0$ of $1 \times 10^{-4}$/cm or less, preferably of $0.5 \times 10^{-4}$/cm or less at a wavelength of 193 nm. Optical elements having such a subaperture ratio are optical elements near the pupil or intermediate optical elements, i.e. elements whose distance from a pupil plane is comparatively small, such that the thermal lens has a particularly unfavorable effect on the imaging or on the wavefront deformation, for which reason these optical elements should have an absorption coefficient as low as possible (in comparison with the further optical elements of the arrangement).

The subaperture ratio assumes values of between 0 and 1, wherein the subaperture ratio assumes the value 1 in a pupil plane and the value 0 in a field plane. For an optical system which images an object field with a maximum object height under a given aperture onto an image field, e.g. a projection lens for microlithography, the subaperture ratio is defined as follows:

$$|R-H|/(R-H|+|H|),$$

where, on the basis of an object point of maximum object height, R is the marginal ray height and H is the chief ray height, and these ray heights are measured in a given plane that is parallel to a pupil plane of the optical system.

In a further embodiment, at least one optical element arranged upstream of a first pupil plane or downstream of a second pupil plane, (in the entire volume) at a wavelength of 193 nm, has an absorption coefficient $k_0$ of $1 \times 10^{-4}$/cm or less, preferably of $0.5 \times 10^{-4}$/cm or less. Particularly in the case of a projection lens, optical elements situated near the entrance (upstream of the first pupil plane) and near the exit (downstream of the second pupil plane) should have a low absorption coefficient in order to minimize the dynamic wavefront deformations, i.e. the wavefront deformations established during the heating of optical elements to the operating temperature.

Alternatively or additionally it is expedient if those optical elements in the beam path which are arranged far away from active manipulators or correction elements, at a wavelength of 193 nm, have an absorption coefficient $k_0$ which is as low as possible and which is $1 \times 10^{-4}$/cm or less, if appropriate $0.5 \times 10^{-4}$/cm or less. An optical element far away from a manipulator is understood to be an optical element arranged such that at least two, if appropriate at least three, further optical elements are situated between said element and an active correction element.

In a further embodiment, the projection lens given a throughput of at least 200 wafers/h, preferably of at least 250 wafers/h, having a respective diameter of 300 mm and a resist sensitivity of 33 mJ/cm$^2$, has an uncorrected dynamic wavefront deformation of less than 80 nm PV, preferably of less than 50 nm PV, in particular of less than 20 nm PV. The dynamic wavefront deformation of the projection lens arises, inter alia, as a result of the temperature-dictated index variation (thermal lens) during the heating of its optical elements during the exposure operation of a projection exposure apparatus into which the projection lens is incorporated. In this case, the irradiation intensity per unit time and thus the heating of the optical elements increase with the throughput of the projection lens or the throughput of the lithography apparatus. In this case, the above numerical values apply to an exposure wavelength of 193 nm and a projection lens for immersion lithography having an image-side numerical aperture of more than 1.3.

In order, even in the case of a high throughput, to keep the (uncorrected) wavefront deformation within the limits indicated above, using the measuring method described above the optical elements of the projection lens are selected such that their location-dependent absorption distribution under the irradiation conditions at the location of use in total leads to temperature-dictated index variations which produce a wavefront deformation of the projection lens within the range indicated above. The uncorrected wavefront deformation is understood to be a deformation which is not corrected by active manipulators that act on the optical elements during the exposure in order to dynamically correct the wavefront deformations. If manipulators of this type are additionally used, the wavefront deformation or the wavefront swing can, if appropriate, additionally be reduced by approximately one to two orders of magnitude.

Further features and advantages of the invention are evident from the following description of exemplary embodiments of the invention, with reference to the figures of the drawing showing details essential to the invention, and from the claims. The individual features can be realized in each case individually by themselves or as a plurality in any desired combination in a variant of the invention.

BRIEF DESCRIPTION OF THE DRAWINGS

Exemplary embodiments are illustrated in the schematic drawing and are explained in the description below. In the figures.

DETAILED DESCRIPTION OF EXEMPLARY EMBODIMENTS

Figure 1A:
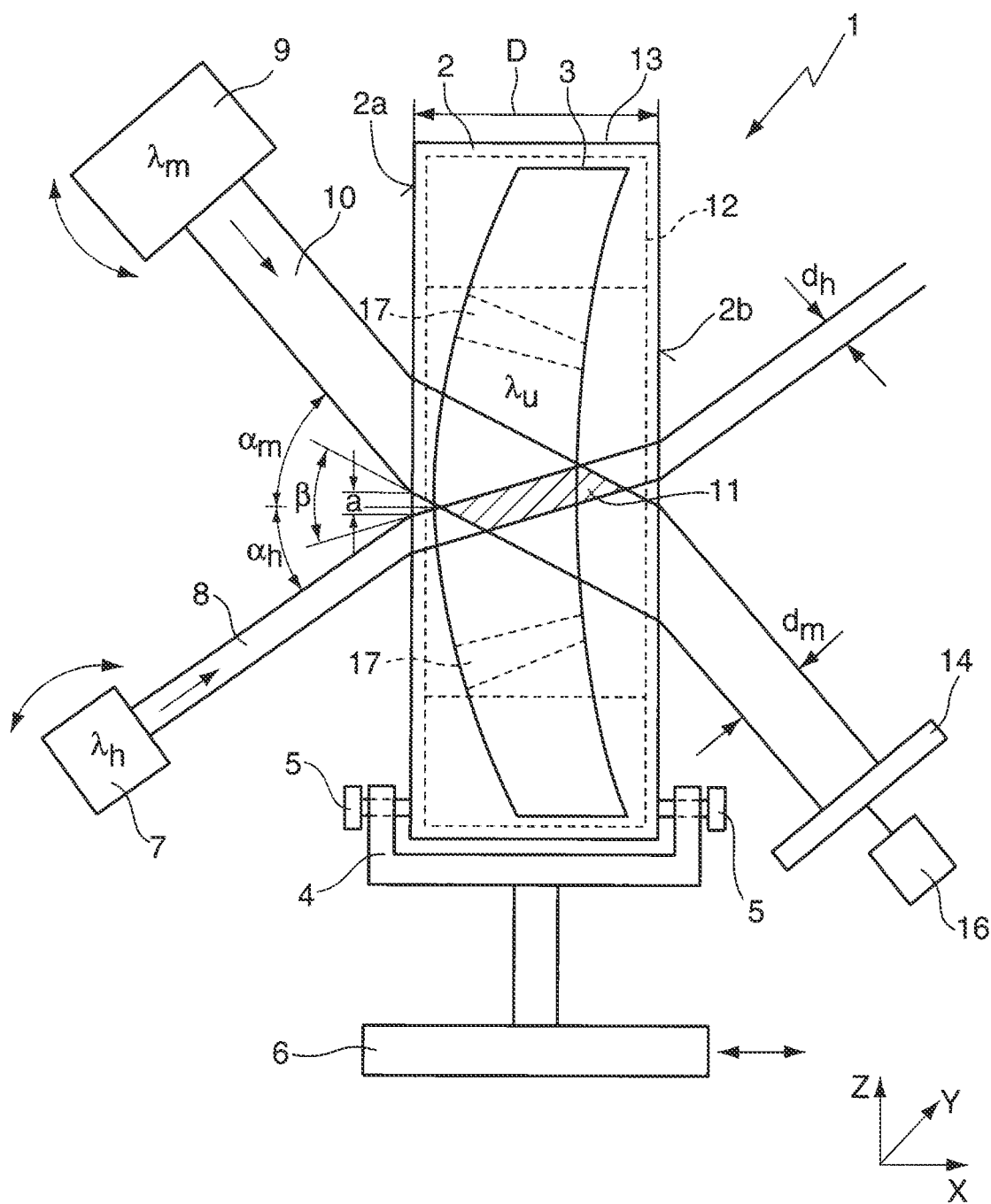
FIGS. 1a,b show schematic illustrations of a first embodiment of an apparatus according to the invention for measuring the absorption in a blank, FIGS. 2a,b show schematic illustrations of the wavefront deformation measured at a detector area from FIG. 1 in a plan view and in a section.

FIG. 1a schematically illustrates an apparatus 1 for determining the absorption of a blank 2 for producing an optical element 3. Said apparatus has a holding device 4 (sample holder) for the blank 2, on which the latter is mounted in an upright fashion and fixed with the aid of adjusting screws 5. The end faces 2a, 2b of the cylindrical blank 2 are provided with a visible polish, i.e. the end faces 2a, 2b have a residual roughness having a polishing quality in the range of the polishing class P1 or P2. The sample holder 4 is arranged on a displacing table 6, which, with the aid of linear drives, enables a displacement—indicated by a double-headed arrow—of the blank 2 in three axial directions X, Y, Z perpendicular to one another. It goes without saying that the apparatus 1 can, if appropriate, also be used for measuring a ground and polished optical element 3.

The apparatus 1 furthermore has a heating light source 7 for generating a (collimated) heating light ray 8 for heating the blank 2. In this case, the wavelength $\lambda_h$ of the heating light ray 8 corresponds, apart from approximately 5 nm, to the used wavelength $\lambda_u$ of the optical element 3, i.e. the operating wavelength of an optical arrangement in which the optical element 3 is intended to be operated. An excimer laser is typically used as the heating light source 7, which laser can have a wavelength $\lambda_h$ of e.g. 248 nm, 193 nm, 176 nm or 157 nm. If a heating light source having a wavelength $\lambda_h$ of 193 nm or less is used, the measurement should be carried out in an inert gas environment, e.g. in a nitrogen environment, wherein the residual oxygen content in the inert gas environment should generally be less than approximately 50 ppm. In this case, the exact value of the residual oxygen content is dependent on the ray paths in the inert gas environment.

The apparatus 1 additionally has a measurement light source 9 for generating a measurement light ray 10 at a wavelength $\lambda_m$ of 639 nm, which likewise passes through the blank 2 and meets the heating light ray 8 at an angle β in an overlap region 11 in the volume of the blank 2. In this case, the overlap region 11 runs within a volume region 12 which is used for producing the optical element 3 and which runs at a distance of at least 5 mm from the end faces 2a, 2b and a lateral surface 13 of the blank 2. That part of the blank 2 which is near the surface and lies outside the volume region 12 was contaminated by impurities during the production of the blank 2 and therefore has a high absorption, such that it is not used for producing the optical element 3.

The heating light ray 8 typically has a diameter $d_h$ of between approximately 2 and 10 mm, while the measurement light ray 10 is expanded and has a diameter $d_m$ that can be at least three times, generally five times, the diameter $d_h$ of the heating light ray, that is to say that the following holds true: $d_m \div 3 \, d_h$ or $\geq 5 \, d_h$, where this ratio strictly speaking relates to the dimension of the measurement light ray 10 transversely with respect to the connecting line (strictly speaking with respect to the connecting plane) between the measurement light ray 10 and the heating light ray 8 in the blank 2. Such a ratio is of advantage in order that a wavefront deformation of the measurement light ray 10 brought about by the heating light ray 8 can be measured in a spatially resolved fashion on a wavefront detector in the form of a Shack-Hartmann sensor 14. Since strictly speaking the dimension of the measurement light ray 10 transversely with respect to the connecting plane is of importance for the ratio, the measurement light ray 10 can also deviate from a circular cross section and have e.g. an elliptical or a rectangular cross section.

In order that the overlap region 11 becomes situated at a desired position within the blank 2, it is necessary for the measurement light ray 10 and the heating light ray 8 to be oriented in a suitable manner. In order to obtain an overlap region 11 lying substantially centrally in the blank 2, which has a thickness D of approximately 50 mm in the present example, firstly the optimum irradiation duration should be known, which is dependent on the sensor 14 used. If the sensor 14 or the camera used therein is comparatively slow, a long irradiation time is chosen, which has the effect that the irradiation or temperature profile in the blank 2 changes radially and axially during the measurement, wherein the heat distribution in the blank drifts by approximately 5 mm in three seconds.

With a sensor 14 in which a conventional 8-10 bit digital camera is used, this is possibly problematic or very many measurement cycles are required. Therefore, the use of a fast camera having 14-16 bit resolution is recommended.

For the following example, therefore, a minimum distance a of the measurement light ray 10 from the heating light ray 8 on the first polished surface 2a of approximately 5 mm was taken as a basis, wherein the diameter $d_h$ of the heating light ray 8 was 3 mm and the diameter $d_m$ of the measurement light ray 10 was 10 mm. The refractive index of the synthetic quartz glass of which the blank 2 consists in the present example is $n_h$=1.560 at the wavelength $\lambda_h$=193 nm of the heating light ray 8 and $n_m$=1.456 at the wavelength $\lambda_m$=639 nm of the measurement light ray 10.

In the example shown in FIG. 1a, the angle $\alpha_m$ of incidence of the measurement light ray 10 is approximately 20° and the angle $\alpha_h$ of incidence of the heating light ray 8 is approximately 19°, such that the two rays 8, 10 intersect in the interior of the blank 2 at an angle β of approximately 28°, while the rays 8, 10 form an angle of $\alpha_m + \alpha_h$ of approximately 38° with one another in the inert gas environment. It goes without saying that the angles $\alpha_m$, $\alpha_h$ of the measurement light ray 10 and of the heating light ray 8 can be varied independently of one another. The propagation direction of the measurement light ray 10 and/or of the heating light ray 8 can likewise be reversed.

In order to increase the resolution in the xy- or z-direction during the measurement, the diameter $d_m$ of the measurement light ray 8 can be reduced and/or larger angles $\alpha_m$, $\alpha_h$ of incidence can be chosen. The maximum expedient intersection angle β at which the two rays 8, 10 meet one another in the interior of the blank 2 is typically less than approximately 40°, if appropriate less than 30° and should generally not be chosen to be less than approximately 15° or than approximately 10°.

Figure 1B:
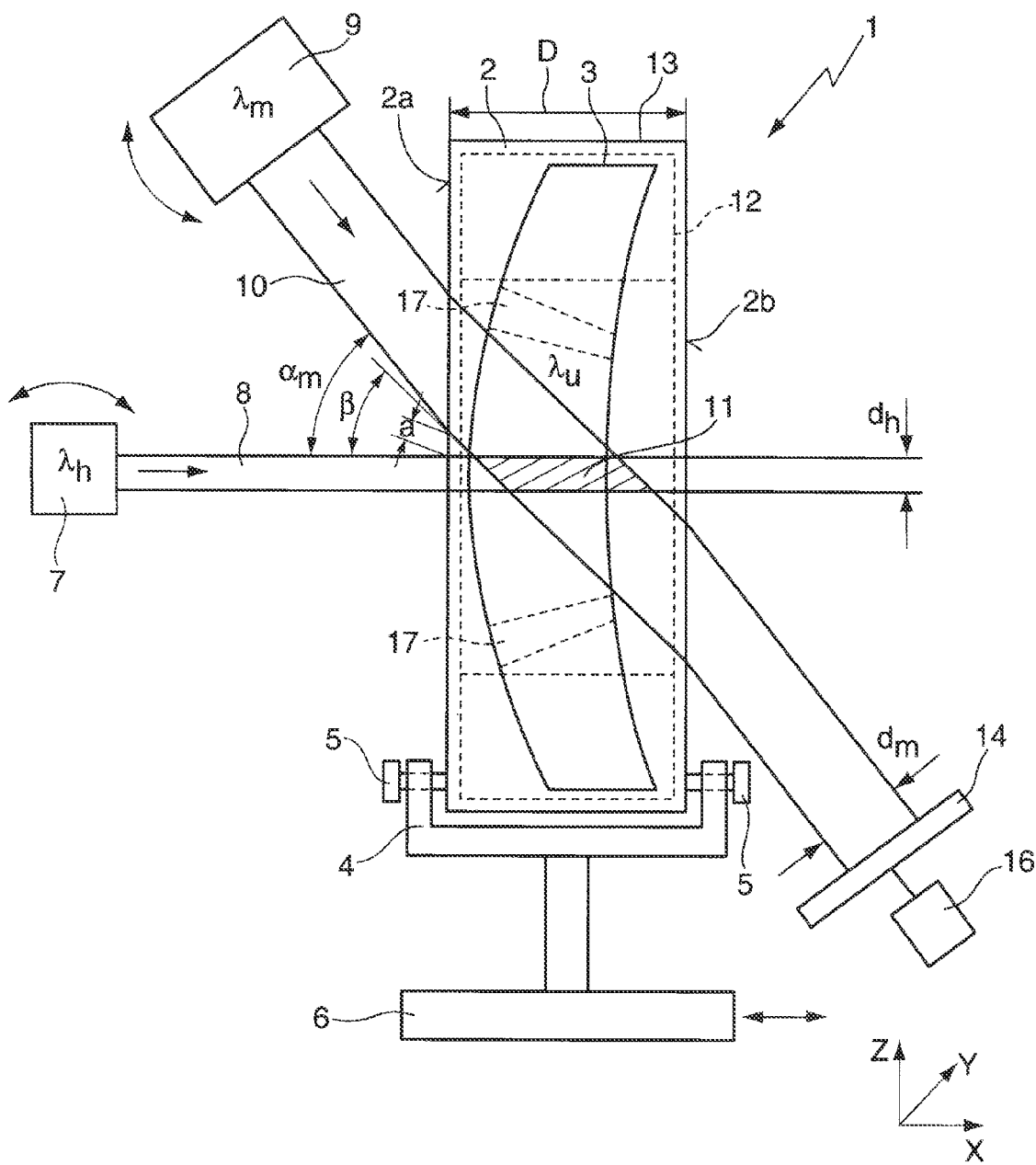

FIG. 1b shows the apparatus 1 in an operating state in which the heating light ray 8 impinges on the first polished surface 2a perpendicularly. In order to comply with the minimum distances of approximately 5 mm from the surfaces 2a, 2b and to obtain an overlap region 11 lying approximately symmetrically in the center of the blank 2 in the thickness direction, an angle $\alpha_m$ of incidence of the measurement light ray 10 of approximately 42° is required in this example, which leads to an intersection angle β of the two rays 8, 10 in interior of the blank 2 of approximately 27°. It goes without saying that the angles shown in FIGS. 1a,b are not identical to the values indicated here and serve merely for illustrating the method. If, in the example shown in FIG. 1b, the angle β between the rays 8, 10 is increased, the volume of the overlap region 11 decreases, such that the distance a between the rays 8, 10 can be increased or there is a limited scanning possibility in the z-direction.

In this case, the wavefront deformation of the measurement light ray 10 is determined by the wavefront of the measurement light ray 10 firstly being measured with the heating light ray 8 switched off. The heating light ray 8 is then switched on and the wavefront is measured anew, wherein the measurements with and without the heating light ray 8 integrate in each case over a few seconds and take place one after the other in less than 1 minute.

Figure 2A:
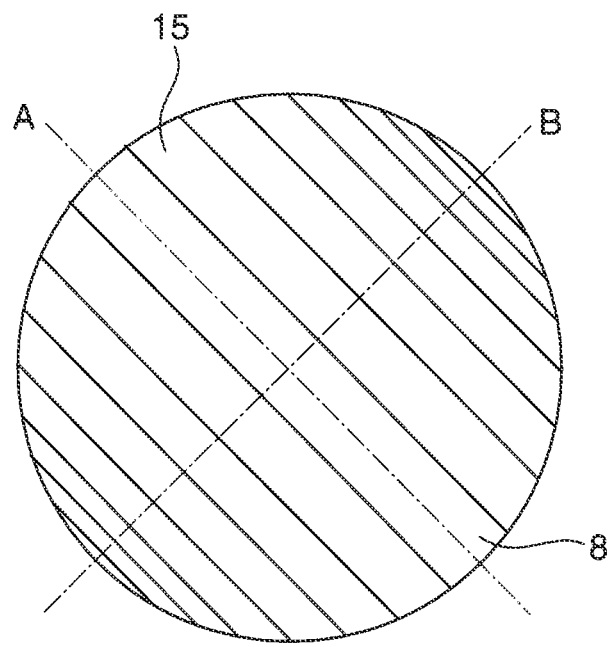
Figure 2B:
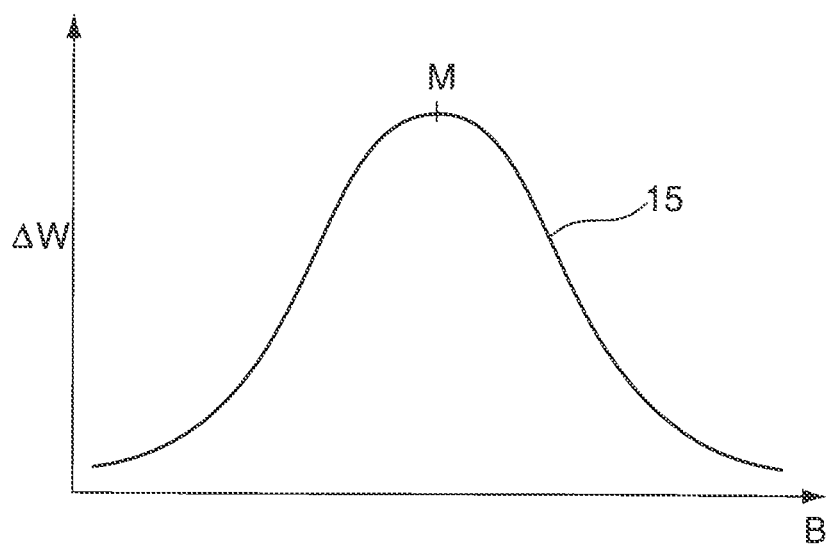

FIG. 2a shows a resultant circular difference image 15 of the wavefront in a plan view, in which case a rectangular or differently shaped difference image 15 can also arise depending on the sensor or evaluation software used. The highest wavefront distortion arises along the line A, which coincides with the image of the heating light ray 8 on the detector area. As the distance from the line A increases, the wavefront distortion decreases, as is indicated by differently spaced lines in FIG. 2a. FIG. 2b shows a section through the wavefront image 15 along the line B, that is to say perpendicular to the heating light ray 8. A maximum M of the wavefront deformation ΔW at the location of the heating light ray 8 and a decrease on both sides of the maximum M can be discerned.

In the measuring method described here, a planar measurement of the wavefront transversely with respect to the heating light ray 8 is thus performed. This makes it possible to dispense with careful alignment during the orientation of the respective rays and instead to perform a suitable software-based evaluation in an evaluation device 16 connected to the Shack-Hartmann sensor 14.

For this purpose, firstly the ray position of the heating light ray 8 on the detector area should be determined using a suitable matching (fit). The signal-to-noise ratio can furthermore be improved by averaging along the axis A parallel to the measurement light ray 8. The result is an averaged sectional image corresponding, in principle, to the illustration in FIG. 2a. As a measure of the absorption, it is possible to determine the height of the maximum M (cf. FIG. 2b) or the gradient or the curvature at a specific distance from the maximum M. Alternatively, a mathematically or experimentally determined distribution function could also be matched to the section illustration of the wavefront deformation ΔW shown in FIG. 2b.

Ideally, the wavefront is evaluated approximately 5 to 30 seconds after the heating light source 7 has been switched on, since gradients and curvatures of the wavefront image 15 are then still clearly defined. As the irradiation duration increases, the wavefront image 15 blurs more and more. In addition, asymmetries become involved if the overlap region 11 approaches as close as a few centimeters from the edge of the blank 2.

In order to increase the signal-to-noise ratio, it is also possible to employ periodic excitation, that is to say that the heating light source 7 is switched on e.g. for 10 seconds and then rests for approximately 1 to 2 minutes. Wavefronts are recorded in each case shortly before and at the end of the irradiation, the difference images then being averaged over a plurality of measurements.

In order to minimize material ageing and nonlinear absorption effects, not only the wavelength $\lambda_h$ but also the irradiation parameters of the heating light ray 8 should be as close as possible to the use conditions (e.g. pulse repetition rate 2 to 8 kHz, energy density $\ll 1$ mJ/cm$^2$, pulse duration 100 to 200 ns (TIS) for $\lambda=193$ nm). In the case of objective lenses as optical elements 3 which are subjected only to low radiation loading, if appropriate the energy density cannot be chosen to be as low as prevails subsequently in the projection lens, since in this case the thermal measurement signal would turn out to be too small. In this case, it is possible to effect a measurement at different energy densities, which is then extrapolated to the energy density that prevails during the operation of the optical element 3.

In general, it holds true here that the ageing of the optical element is proportional to the energy density^2*pulse number/pulse duration. At every location of the optical element, the total loading during the measurement should be less than approximately 1/10 of the value to be expected over the lifetime of the optical element 3. This proportion seems high, but during operation many optical elements are only subjected to energy densities of single μJ/cm$^2$, while expedient energy densities for the measurement are typically in the range of between approximately 200 and 1000 μJ/cm$^2$.

If the intention is to wait until the end of cleaning effects and/or bleaching effects in the material of the blank 2 before the measurement, firstly it is possible to determine a necessary prior irradiation dose with use of repeated measurements at an individual measurement point (until the absorption does not fall rapidly, but rather only rises very slowly as a result of material ageing). In a second step, all desired measurement locations can then be irradiated with the dose thus determined, before the beginning of the measurement.

On account of the detected measurement signal being largely independent of the alignment of the measurement light ray 10 and/or of the heating light ray 8 and of the distance from the lateral surface 13 and/or from the end faces 2a, 2b, the blank 2 can be scanned in the X- and Y-directions in the optically used volume 12, for which purpose the displacing table 6 is correspondingly driven with a control unit (not shown). In addition, for orienting the measurement light ray 10 the measurement light source 9, or for orienting the heating light ray 8 the heating light source 7, can be rotated by a suitable movement mechanism, as is indicated by corresponding double-headed arrows. It goes without saying that, if appropriate, a linear displacement of the measurement light source 9 or of the heating light source 7 can also be effected. Given a small overlap region 11 (interaction volume) between the measurement light ray 10 and the heating light ray 8, a spatially resolved measurement can also be effected in the Z-direction, i.e. parallel to the cylinder axis of the blank 2, such that it is possible to record a depth profile of the absorption within that volume of the blank 2 which is used for producing the optical element 3.

In this way, the absorption can also be measured nondestructively in those partial regions 17—indicated by dashed lines—of the blank 2 in which the thermal lens, i.e. the change in the refractive index with temperature, has a particularly unfavorable effect on the (imaging) properties of the optical element 3. In these critical partial regions 17, the absorption coefficient $k_0$ of the volume absorption of the optical element 3 should be $0.5 \times 10^{-4}$/cm or less, preferably $0.2 \times 10^{-4}$/cm or less, in particular $0.1 \times 10^{-4}$/cm or less. Outside said partial regions 17, the absorption coefficient $k_0$ can be greater, but should not exceed a value of $2 \times 10^{-4}$/cm, preferably of $1 \times 10^{-4}$/cm, in particular of $0.5 \times 10^{-4}$/cm, anywhere in the optical element 3.

With the spatially resolved measurement method described above, it is thus possible to ascertain whether the blank 2 is suitable for producing an optical element 3 which meets the requirements made for use in an optical arrangement with regard to absorption. In particular, it is also possible to perform an assignment between the blank 2 and optical elements 3 which can be produced therefrom and which can fulfill the above specifications with regard to absorption on account of their geometry or their positioning in an optical arrangement. It goes without saying that, if appropriate, the blank can also have a location-dependent absorption which is on no account suitable for producing optical elements.

Figure 3:
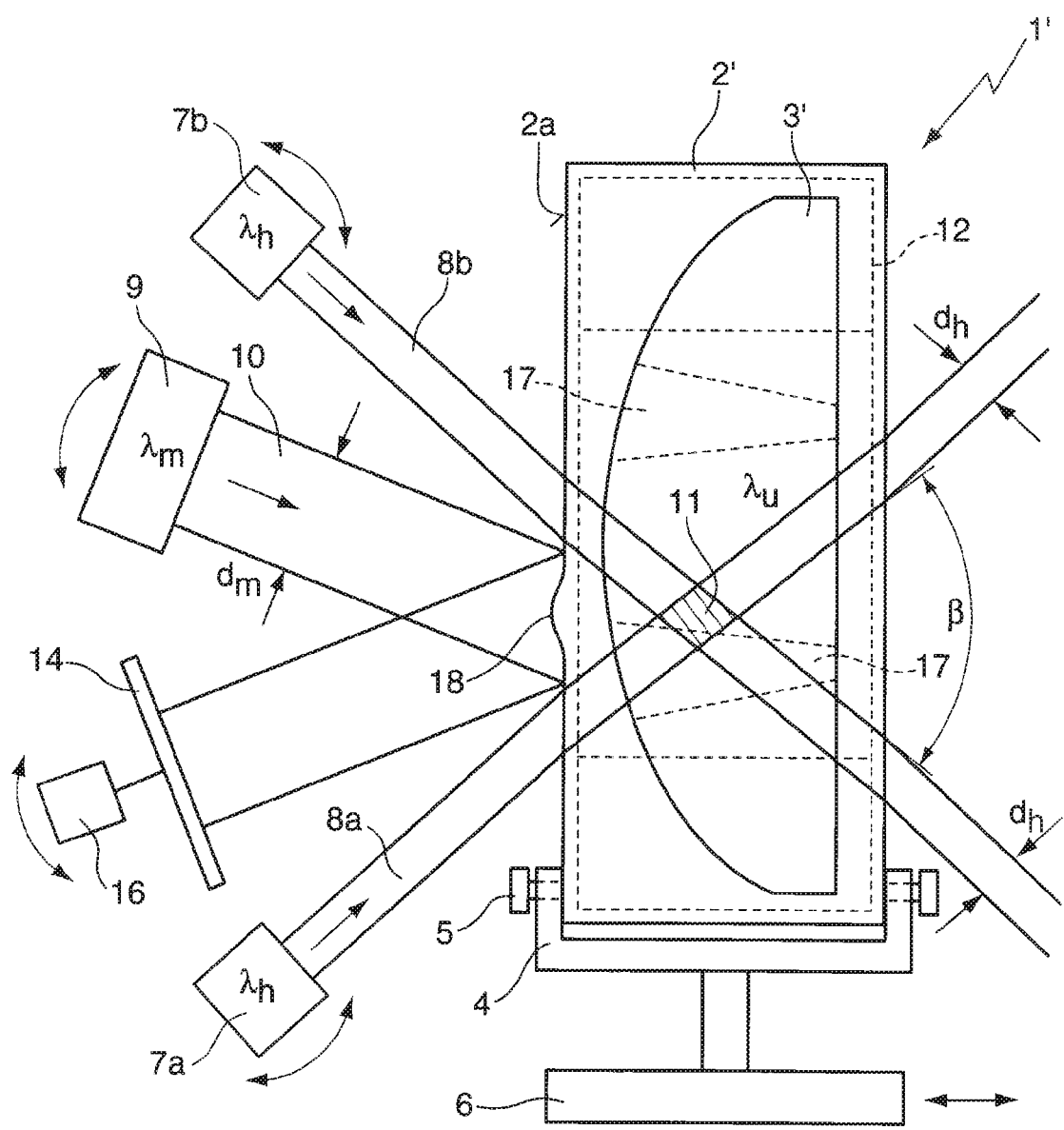
FIG. 3 shows a schematic illustration of a further embodiment of the apparatus, wherein the absorption is determined with a reflected measurement light ray.

FIG. 3 shows an apparatus 1' having, in contrast to the apparatus 1 shown in FIG. 1, two heating light sources 7a, 7b for generating two heating light rays 8a, 8b. In the case of the apparatus 1' shown in FIG. 3, it suffices if only one end face 2a of the blank 2' is provided with a visible polish. The two heating light rays 8a, 8b are caused to overlap in a volume that is near the surface and is used for the production of an optical element 3'. In this case, the heating in the overlap region 11 is greater than the heating along the individual heating light rays 8a, 8b. As a result of the heating, a protuberance, designated hereinafter as bulge 18 and illustrated with a greatly exaggerated extent in FIG. 3, forms at the end face 2a of the blank 2'.

The measurement light ray 10 generated by the measurement light source 9 impinges on the end face 2a of the blank 2' in the vicinity of the bulge 18, as a result of which a wavefront distortion arises which is detected with the Shack-Hartmann sensor 14 on the measurement light ray 10 reflected from the end face 2a. As is illustrated in FIG. 3, the measurement light ray 10 ideally has a diameter $d_m$ that is small enough that it does not encompass the two entrance regions of the heating light rays 8a, 8b at the end face 2a of the blank 2', since considerable heating occurs there on account of the surface absorption.

As an alternative to the detection of the reflected measurement light ray 10, the measurement light ray 10 could also be oriented such that it only strikes the flank of the bulge 18 and is deflected from there. The measurement light ray 10 could also run parallel to the end face 2a and be deflected by the heating of the air, the measurement in the latter case being effected by the so-called PTD or Mirage method. However, the use of a wavefront sensor has the advantage over these detection methods that careful alignment of the rays is not necessary or can be replaced by software adaptation. It goes without saying that, in the case of the apparatuses 1, 1' shown in FIGS. 1 and 3, respectively, it is also possible to use more than two heating light rays in order to increase the local index gradient and thus to improve the signal-to-noise ratio.

In the manner described above it is possible to identify blanks 2, 2' which are suitable for producing optical elements 3, 3' which, with regard to absorption, satisfy the requirements for use in a projection exposure apparatus 101 for microlithography, which is described in greater detail below in connection with FIG. 4. In this case, the measurement method can be used to optimize the production process for the blank 2, 2' and to determine the spatial distribution of the absorption in the respective blank 2, 2'. After the optimization of the production process it suffices to employ a statistical process control or, if appropriate, to carry out a measurement only at one to approximately three characteristic locations on each blank.

The microlithographic projection exposure apparatus 101 serves for producing highly integrated semiconductor components using immersion lithography. It comprises, as light source, an excimer laser 103 having an operating wavelength of 193 nm. Alternatively, light sources having other operating wavelengths, for example 248 nm or 157 nm, could also be used. A downstream illumination system 105 generates, in its exit plane or object plane 107, a large, sharply delimited, very homogeneously illuminated illumination field adapted to the telecentricity requirements of the downstream projection lens 111. The illumination system 105 has devices for controlling the pupil illumination and for setting a predefined polarization state of the illumination light. In the beam path downstream of the illumination system 105, a device (reticle stage) for holding and moving a mask 113 is arranged such that the latter lies in the object plane 107 of the projection lens 111 and is movable in said plane for scanning operation in a driving direction 115.

The projection lens 111 follows downstream of the object plane 107, also designated as mask plane, said projection lens imaging an image of the mask with a reduced scale onto a substrate 119, for example a silicon wafer, said substrate being covered with a photoresist, also called resist 121. The substrate 119 is arranged such that the planar substrate surface with the resist 121 substantially coincides with the image plane 123 of the projection lens 111. The substrate is held by a device 117 comprising a drive for moving the substrate 119 synchronously with the mask 113. The device 117 also comprises manipulators for moving the substrate 119 both in the z-direction parallel to the optical axis 125 of the projection lens 111 and in the x- and y-directions perpendicular to said axis.

The device 117 (wafer stage) provided for holding the substrate 119 is designed for use in immersion lithography. It comprises a receptacle device 127, which is movable by a scanner drive and the base of which has a flat cutout for receiving the substrate 119 (wafer). By virtue of a circumferential edge 129, a flat, upwardly open, liquid-tight receptacle for an immersion liquid 131 is formed. The height of the edge is dimensioned such that the introduced immersion liquid 131 can completely cover the substrate surface with the resist 121 and the exit-side end region of the projection lens 111 can dip into the immersion liquid 131 with a correctly set working distance between lens exit and substrate surface 121.

The projection lens 111 has a virtually hemispherical planoconvex lens element 133 as the last optical element closest to the image plane 123 and arranged downstream of a second pupil plane 138b, the exit surface 135 of said planoconvex lens element being the last optical surface of the projection lens 111. The exit side of the last optical element is completely immersed in the immersion liquid 131 during the operation of the projection exposure apparatus 101 and is wetted by said liquid. The planoconvex lens element 133, in the same way as a further lens element 137 arranged in the vicinity of a first pupil plane 138a in the projection lens 111, can be formed by an optical element 3' or 3 as shown in FIG. 1 or in FIG. 3.

On the basis of the absorption behavior determined in a spatially resolved fashion in the manner described above, it is possible to create a model for the temperature- and location-dependent refractive index variation Δn in the respective optical element 133 or 137 during the operation of the projection lens 111. For this purpose, it is necessary to know the radiation intensity at the location of the respective optical element 133, 137, which can be determined using suitable computation methods or experimentally. If appropriate, on the basis of the thermal lens determined in this way, it is possible to alter the position of the optical element 133, 137 in the projection lens 111 or the entire design of the projection lens 111 or of the projection exposure apparatus 101 such that, with predefined location-dependent absorption of the respective optical element 133, 137, the refractive index variation Δn brought about by the illumination radiation during operation—even in the case of different illumination modes—at every location of the respective optical element 133, 137 is chosen such that, given a throughput of at least 200 wafers/h, in particular 250 wafers/h, the projection lens 111 has a wavefront deformation not corrected by active manipulators in the image plane 123 of less than approximately 80 nm, if appropriate of less than approximately 50 nm, in particular of less than approximately 20 nm, peak-to-valley, as is described in greater detail below in connection with FIG. 5 and FIG. 6.

Figure 5:
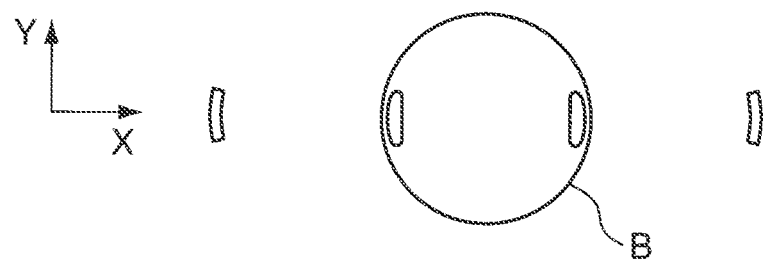
FIG. 5 shows an illustration of a dipole illumination distribution at the entrance of a projection lens shown in FIG. 4.

FIG. 5 shows an angular distribution directly downstream of the mask 113, wherein the illustration shows the sine of the propagation angle in the xy-plane, wherein the axes (not shown) extend from −1 to +1. In the present example, the illustration shows a dipole distribution with a dipole extending over an angle of approximately 35° and running in the horizontal (x-)direction for a full numerical aperture NA of 1.35 using an aperture ratio σ of 0.85-0.95. The angular distribution shown in FIG. 5 is a conventional dipole distribution such as is used for the production of patterned semiconductor components e.g. in the form of NAND flash or DRAM chips. In FIG. 5, it is possible to clearly discern the two poles near the maximum propagation angle, which is limited by the numerical aperture B (stop) illustrated as a circle. The poles lying further outward are higher diffraction orders that are no longer imaged by the projection lens 111.

Figure 6:
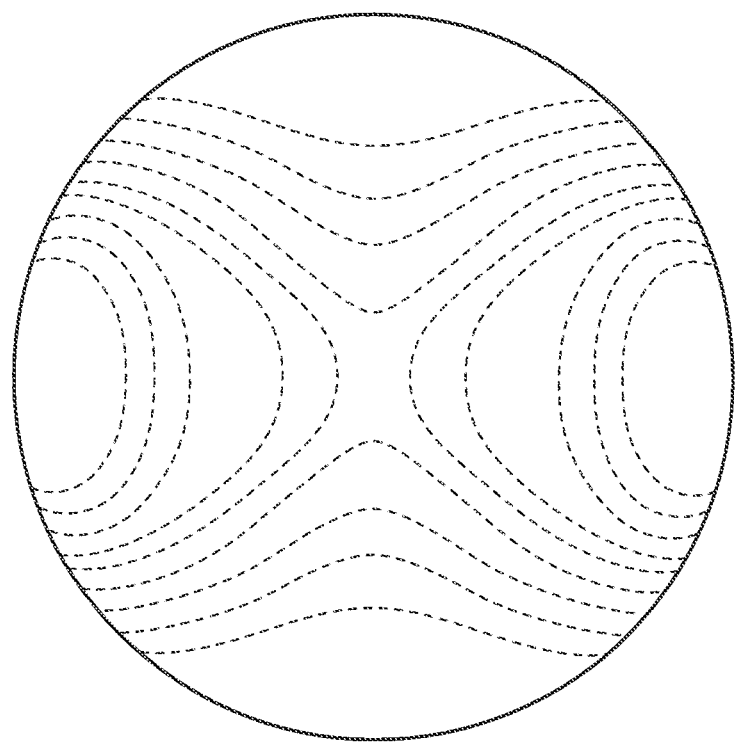
FIG. 6 shows an illustration of the wavefront deformations in the image plane in the case of the dipole illumination distribution from FIG. 5.

FIG. 6 shows the associated (simulated) wavefront aberration in the image plane 123 for a throughput of approximately 250 to 300 wafers per hour with a respective wafer diameter of 300 mm and a resist having a sensitivity of 33 mJ/cm², wherein, for the optical elements of the projection lens 111, an absorption coefficient $k_0$ of at most $2\times10^{-4}$ was assumed and, at particularly critical optical elements, an absorption coefficient $k_0$ of at most $1 \times 10^{-4}$ was assumed, to be precise in each case at a wavelength of 193 nm. The peak-to-valley value of the uncorrected dynamic wavefront deformation illustrated in FIG. 6 was less than 80 nm in the simulation.

Figure 4:
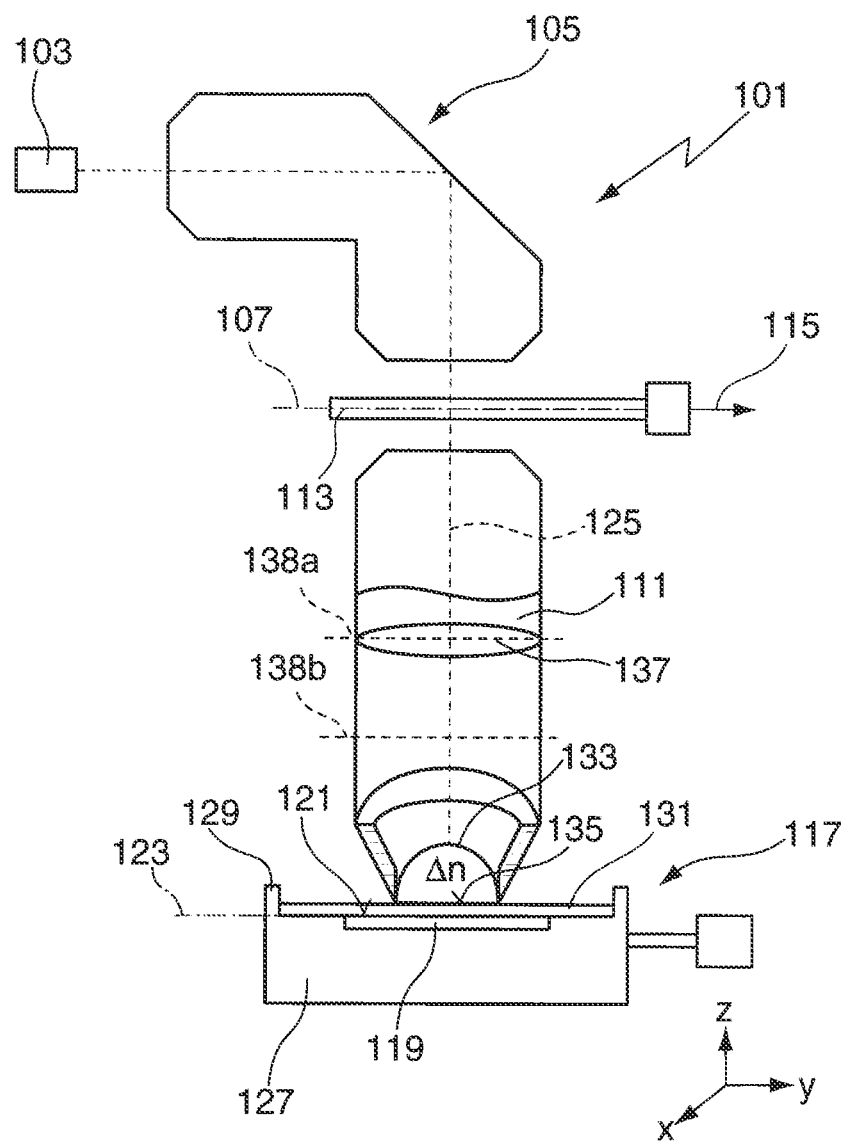
FIG. 4 shows a schematic illustration of a projection exposure apparatus for microlithography comprising optical elements measured with the apparatuses shown in FIGS. 1 and 3, respectively.

To summarize, the absorption can be determined in a spatially resolved fashion in the manner described above for all optical elements which are intended to be used in an optical arrangement, that is to say that the procedure described above or the optimization described above is possible not only in the case of the projection lens 111, but also in the case of other optical arrangements, e.g. in the case of the illumination system 105 illustrated in FIG. 4.

In this case, proceeding from the known absorption distribution and the resultant optical properties of the optical elements during the production of the optical arrangement it is possible to optimize the optical design with regard to the individual properties of the optical elements, that is to say that the relative position of the optical elements or the assignment of the blanks to specific lens element positions can be set during assembly such that the optical properties, in particular the imaging properties of the overall system are optimized.

By way of example, in the case of such an optimization at lens element positions situated intermediately or near to a pupil plane 138a, 138b of the projection lens 111, i.e. at lens element positions at which the subaperture ratio is more than 50%, if appropriate more than 70%, in particular more than 80%, it is possible to use a lens element material which, in the entire optically relevant volume, has an absorption coefficient $k_0$ of less than $1 \times 10^{-4}$/cm, if appropriate even of $0.5 \times 10^{-4}$/cm.

An absorption coefficient lying in this range of values has also proved to be of advantage in the case of optical elements which are arranged in the beam path upstream of the first pupil plane 138a and downstream of the second pupil plane 138b, that is to say e.g. for the lens element 133 serving as a termination element. It is also of advantage for optical elements at lens element positions far away from active manipulators, i.e. between which and an active manipulator two or three further optical elements are situated, to choose a material having a low maximum absorption coefficient that is likewise within the range of values indicated above.

The above description of various embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. Method for determining absorption of a blank provided for producing an optical element, comprising:
   radiating a heating light ray through the blank for heating the blank, and determining the absorption in the blank by measuring at least one property of a measurement light ray influenced by the heating of the blank, wherein either the heating light ray and the measurement light ray or the heating light ray and a further heating light ray are oriented to enter into the blank through a first polished surface or a second polished surface situated opposite the first surface, and to meet one another exclusively in an overlap region in an interior of the blank at which the measurement light ray and the heating light ray or the two heating light rays meet one another.

2. Method according to claim 1, wherein the heating light ray and the measurement light ray or the two heating light rays meet one another in the interior of the blank at an angle ($\beta$) of less than 90°.

3. Method according to claim 2, wherein the angle ($\beta$) is less than 30°.

4. Method according to claim 1, wherein, as a property of the measurement light ray, a wavefront deformation ($\Delta W$) of the measurement light ray brought about by the heating light ray is measured in a spatially resolved manner.

5. Method according to claim 4, wherein the wavefront deformation is measured with a Shack-Hartmann sensor.

6. Method according to claim 1, wherein the position of the overlap region at is varied in the volume used for the production of the optical element in at least two dimensions (X, Y), (X, Y, Z), in order to determine the spatially resolved absorption behavior in the blank.

7. Method according to claim 6, further comprising creating a model for the temperature-dependent refractive index variation ($\Delta n$) of the optical element from the blank from the spatially resolved absorption behavior in the blank.

8. Method according to claim 1, wherein the measurement light ray has a rectangular or an elliptical cross section.

9. Method according to claim 1, wherein the measurement light ray and the heating light ray are at a distance (a) of at least 5 mm from one another on the first and the second polished surfaces.

10. Method according to claim 1, wherein at least one property of the measurement light ray deflected by the polished surface in a region in between the two heating light rays is measured.

11. Method according to claim 1, wherein the wavelength ($\lambda_h$) of the heating light ray deviates from the used wavelength ($\lambda_u$) of the optical element by less than 5 nm, wherein the used wavelength ($\lambda_u$) is 250 nm or less.

12. Method according to claim 1, wherein the wavelength ($\lambda_m$) of the measurement light ray deviates from the wavelength ($\lambda_h$) of the heating light ray by more than 250 nm.

13. Method according to claim 1, further comprising:
   irradiating the blank with a predefined radiation dose before determining the absorption of the blank.

14. Method according to claim 1, wherein an optical element is produced from blanks in which, in the entire volume used for the production of the optical element, at a wavelength of 193 nm, an absorption coefficient $k_0$ of $2 \times 10^{-4}$/cm or less is measured.

15. Optical element which, in an entire volume thereof, at a wavelength of 193 nm, has an absorption coefficient $k_0$ of $2 \times 10^{-4}$/cm or less, wherein the absorption coefficient $k_0$ is determined by a method according to claim 1.

16. Optical arrangement, comprising at least one optical element according to claim 15.

17. Optical arrangement comprising at least one optical element having a subaperture ratio of greater than 50% at a wavelength of 193 nm, and having an absorption coefficient $k_0$ of $1 \times 10^{-4}$/cm or less, wherein the absorption coefficient $k_0$ is determined by a method according to claim 1.

18. Optical arrangement according to claim 17, configured as a projection lens for microlithography which, given a throughput of at least 200 wafers/hour having a wafer diameter of 300 mm and a resist sensitivity of 33 mJ/cm², has an uncorrected dynamic wavefront deformation of less than 80 nm PV.

19. Optical arrangement according to claim 17, configured as a projection lens for microlithography which, given a throughput of at least 200 wafers/hour having a wafer diameter of 300 mm and a resist sensitivity of 33 mJ/cm² has an uncorrected dynamic wavefront deformation of less than 20 nm PV.

20. Optical arrangement comprising at least one optical element arranged upstream of a first pupil plane or downstream of a second pupil plane, at a wavelength of 193 nm, and having an absorption coefficient $k_0$ of $1 \times 10^{-4}$/cm or less, wherein the absorption coefficient $k_0$ is determined by a method according to claim 1.

21. Method according to claim 1, wherein the interior of the blank is located in a volume of the blank used for production of the optical element.

22. Optical arrangement comprising at least one optical element having a subaperture ratio of greater than 80% at a wavelength of 193 nm, wherein the absorption coefficient $k_0$ is $0.5 \times 10^{-4}$/cm or less, and wherein the absorption coefficient $k_0$ is determined by the method according to claim 1.

23. Apparatus for determining the absorption of a blank for producing an optical element, comprising:
  a holding device for the blank,
  at least one heating light source to generate at least one heating light ray for heating the blank,
  a measurement light source to generate a measurement light ray,
  and a detector unit to measure at least one property of the measurement light ray influenced by the heating of the blank,
wherein either the heating light ray and the measurement light ray or the heating light ray and a further heating light ray are oriented to enter into the blank through a first polished surface or a second polished surface situated opposite the first surface, and to meet one another exclusively in an overlap region in an interior of the blank at which the measurement light ray and the heating light ray or the two heating light rays meet one another.

24. Apparatus according to claim 23, wherein the heating light ray and the measurement light ray or the two heating light rays meet one another in the interior of the blank at an angle ($\beta$) of less than 90°.

25. Apparatus according to claim 23, wherein the holding device for the blank is displaceable linearly in at least two directions (X, Y).

26. Apparatus according to claim 23, wherein the detector unit comprises a Shack-Hartmann sensor configured to measure wavefront deformations.

27. Apparatus according to claim 23, wherein the interior of the blank is located in a volume used for production of the optical element.

28. Apparatus according to claim 23, wherein the angle ($\beta$) is less than 30°.

29. Optical arrangement, configured as a projection lens for microlithography:
  comprising at least one optical element which, in an entire volume thereof has an absorption coefficient $k_0$ of $2 \times 10^{-4}$/cm or less at a wavelength of 193 nm,
  wherein the optical arrangement, given a throughput of at least 200 wafers/hour, each having a wafer diameter of 300 mm and a resist sensitivity of 33 mJ/cm², has an uncorrected dynamic wavefront deformation of less than 80 nm PV, and
  wherein the absorption coefficient $k_0$ is determined by a method for determining absorption of a blank from which the optical element is produced, the method comprising:
    for heating the blank, radiating a heating light ray through the blank, and
    determining the absorption in the blank by measuring at least one property of a measurement light ray influenced by the heating of the blank, wherein either the heating light ray and the measurement light ray or the heating light ray and a further heating light ray are oriented to enter into the blank through a first polished surface or a second polished surface situated opposite the first surface, and to meet one another exclusively in an interior of the blank.

* * * * *

UNITED STATES PATENT AND TRADEMARK OFFICE
CERTIFICATE OF CORRECTION

PATENT NO.         : 9,036,152 B2                              Page 1 of 1
APPLICATION NO.    : 14/150552
DATED              : May 19, 2015
INVENTOR(S)        : Eric Eva It is certified that error appears in the above-identified patent and that said Letters Patent is hereby corrected as shown below:

In the Specification:
Column 6; Line 54-55; delete "Iaserinduzierter" and insert -- laserinduzierter --.

In the Claims:
Column 18; Claim 6; Line 15; delete "at is" and insert -- is --.

Signed and Sealed this
Seventeenth Day of May, 2016

Michelle K. Lee
*Director of the United States Patent and Trademark Office*